United States Patent [19]

Wilkerson et al.

[11] Patent Number: 5,698,559
[45] Date of Patent: Dec. 16, 1997

[54] DISUBSTITUTED POLYCYCLIC SYSTEMS AS COGNITION ENHANCERS

[75] Inventors: Wendell Wilkie Wilkerson; Christopher Allan Teleha, both of New Castle, Del.

[73] Assignee: The DuPont Merck Pharmaceutical Company, Wilmington, Del.

[21] Appl. No.: 620,643

[22] Filed: Mar. 25, 1996

Related U.S. Application Data

[62] Division of Ser. No. 312,488, Sep. 26, 1994, Pat. No. 5,532,249, which is a continuation of Ser. No. 821,571, Jan. 16, 1992, Pat. No. 5,272,269.

[51] Int. Cl.[6] .................. C07D 401/04; C07D 403/04; A61K 31/44; A61K 31/505
[52] U.S. Cl. .................. 514/256; 514/255; 514/292; 544/333; 544/405; 546/84; 546/285
[58] Field of Search .................. 546/84, 285; 514/292, 514/333, 405, 255, 256

[56] References Cited

U.S. PATENT DOCUMENTS

| | | | |
|---|---|---|---|
| 4,760,083 | 7/1988 | Myers et al. | 514/333 |
| 5,173,489 | 12/1992 | Earl et al. | 514/252 |

*Primary Examiner*—Alan L. Rotman
*Attorney, Agent, or Firm*—Gerald J. Boudreaux; David H. Vance

[57] ABSTRACT

Compounds of Formula I have been shown to enhance the release of the neurotransmitter acetylcholine, and thus may be useful in the treatment of diseases of man, such as in Alzheimer's disease and other conditions involving learning and cognition, where subnormal levels of this neurochemical are found.

The compounds of this invention can be described as shown in Formula I

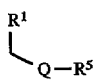

Formula I where Q is

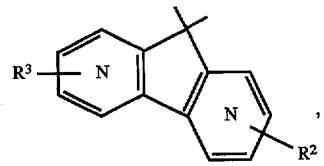

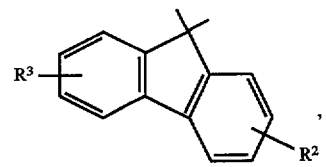

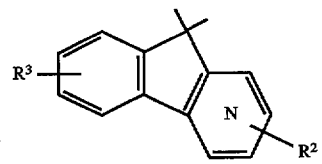

$R^1$ is 4-, 3-, or 2-pyridyl, pyrimidyl, pyrazinyl, or fluoro-4-pyridyl;

$R^2$ and $R^3$ are independently H, F, Cl, Br, $NO_2$, OH, $-R^4$, $-O-R^4$, $-CO_2R^4$, $-COR^4$, $-CONH_2$, $-CONHR^4$, $-CONR_4R^{4'}$, $-S(O)_{m2}-R^4$, $NH_2$, $CF_3$, $NHR^4$, $NR^4R^{4'}$;

$R^4$ and $R^{4'}$ are independently H, alkyl of 1 to 4 carbons, $CH_2$Phe-W or Phe-W;

Phe is a phenyl group;

$R^5$ is $-(CH_2)_n-Y$ or $-OCOR^4$;

Y is H, OH, $NH_2$, $NHR^4$, $NR^4R^{4'}$, $NHCOR^4$, $NHCO_2R^4$, $NHS(O)_2R^4$; F, Cl, Br, $OR^4$, $S(O)_mR^4$, $-CO_2H$, $-CO_2R^4$, $-CN$, $-CONR^4R^{4'}$, $-CONHR^4$, $-CONH_2$, $-COR^4$; $-CH=CHCO_2R^4$, $-OCOR^4$, Phe, Phe-W, $-C\equiv CCO_2R^4$, $-CH=CHR^4$, or $-C\equiv C-R^4$;

W is F, Cl, Br, $R^4$, $OR^4$, $NO_2$, $NH_2$, $NHR^4$, $NR^4R^4$, CN, $S(O)_m-R^4$;

m is 0, 1 or 2;

n is 1 to 7;

and hydrates and physiologically suitable salts thereof.

33 Claims, No Drawings

DISUBSTITUTED POLYCYCLIC SYSTEMS AS COGNITION ENHANCERS

This is a division of application Ser. No. 08/312,488 filed Sep. 26, 1994, now U.S. Pat. No. 5,532,206, which is a continuation of application Ser. No. 07/821,571 filed Jan. 16, 1992, now U.S. Pat. No. 5,272,296.

BACKGROUND OF THE INVENTION

1. Field of the Invention

This invention relates to disubstituted polycyclic compounds, to pharmaceutical compositions thereof, and methods of use in mammals to treat cognitive disorders, neurological dysfunction, and/or mood disturbances such as, but not limited to degenerative nervous system diseases. Additionally, these compounds can be used as reagents in studies on the biochemical mechanism of neurotransmitter based diseases.

2. Background Including Prior Art

Increasingly there is a need for effective treatments for nervous system disorders and neurological deficiencies. Many of these diseases correlate with increasing age due mainly to degenerative changes in the nervous systems. Although in early stages of some diseases, certain systems are rather specifically affected (e.g., cholinergic systems in Alzheimer's Disease and Myasthenia Gravis, the dopaminergic system in Parkinson's Disease, etc.), multiple neurotransmitter system deficiencies (acetylcholine, dopamine, norepinephrine, serotonin) are generally found at later stages of disease such as senile dementia, multi-infarct dementia, Huntington's Disease, mental retardation, etc. This explains the generally observed multiple symptomatology that includes cognitive, neurological, and effective/psychotic components (see Gottfries, Psychopharmacol., 1985, 86, 245). Deficits in the synthesis and release of acetylcholine in the brain are generally thought to be related to cognitive impairment (see Francis, et al., New England J. Med., 1985, 7, 313) whereas neurological deficits (e.g. Parkinsonian symptoms) and mood/mental changes may be related to impairment of dopaminergic and serotonergic systems, respectively. Other neurological deficits (e.g. Myasthenia Gravis) are related to cholinergic deficiencies in the peripheral nervous system.

Treatment strategies employed previously encompass vasoactive drugs like vincamine and pentoxifylline; metabolic enhancers like ergoloid mesylates, piracetam, and naftidrofuryl; neurotransmitter precursors like I-DOPA, choline, and 5-hydroxytryptamine; transmitter metabolizing enzyme inhibitors such as physostigmine; and neuropeptides like adrenocorticotropic hormone and vasopressin-related peptides. Except for I-DOPA treatment for Parkinson's Disease and cholinesterase inhibitor treatment for Myasthenia Gravis, these treatment strategies have generally failed to enhance the residual function of the affected systems by enhancing the stimulus-induced release of neurotransmitters. Theoretically, such an enhancement would improve the signal-to noise ratio during chemical transmission of information, thereby reducing deficits in processes related to cognition, neurological function, and mood regulation.

Saleta, B., et al., Br. J. Clin. Pharmac. (1989), 28, 1–16, suggest that DuP 996 may exhibit indirect action or may have an active metabolite, and that three metabolites have been identified, a mono-N-oxide, a bis-oxide and a C-dealkylated alcohol. However, Chem. Abstracts 111 (13) :108875p suggest that the following structure is one of the above-named metabolites of DuP 996. On the other hand, neither of these references presented chemical data, and we feel it is not possible for this structure to be a metabolite of DuP 996.

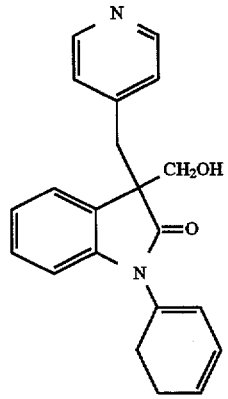

European Patent Application 311,010, published Apr. 12, 1989, discloses that α, α-disubstituted aromatics or heteroaromatics of the formula:

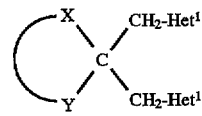

or a salt thereof wherein X and Y are taken together to form a saturated or unsaturated carbocyclic or heterocyclic first ring and the shown carbon in said ring is α to at least one additional aromatic ring or heteroaromatic ring fused to the first ring; one of $Het^1$ or $Het^2$ is 2, 3, or 4-pyridyl; or 2, 4, or 5-pyrimidinyl, and the other is selected from
  (a) 2, 3, or 4-pyridyl
  (b) 2, 4, or 5-pyrimidinyl
  (c) 2-pyrazinyl
  (d) 3 or 4-pyridazinyl,
  (e) 3 or 4-pyrazolyl,
  (f) 2 or 3-tetrahydrofuranyl, and
  (g) 3-thienyl
are useful as cognition enhancers.

U.S. Pat. No. 4,760,083, issued to Myers et al. on Jul. 26, 1998, discloses that indolines of the following formula are useful for treatment of cognitive deficiencies:

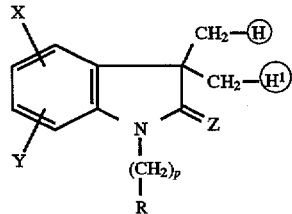

wherein p is 0 or 1; Z is O or S; R is $C_1$–$C_{10}$alkyl, $C_1$–$C_3$ cycloalkyl, 2-pyridyl, 3-pyridyl, 4-pyridyl or

V, W, X and Y are independently halo, $C_1$–$C_3$ alkyl, $OR^1$, $NO_2$, $CF_3$, CN or $NR^2R^2$;

$R^1$ and $R^2$ independently are H or $C_1$-$C_3$ alkyl;

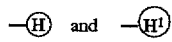

independently are 6-membered heterocyclic aromatic rings containing at least one nitrogen atom as a part of the ring optionally substituted with one substituent selected from the group $C_1$-$C_3$ alkyl, halo, $OR^1$ or $NR^1R^2$, or an N-oxide or pharmaceutically suitable acid addition salt thereof. These references claim the necessity of two heteroaryl groups for activity

SUMMARY OF THE INVENTION

Presently, it has been found that certain polycyclic compounds having "mixed pendent groups" geminal substitutions enhance the stimulus-induced release of neurotransmitters, specifically acetylcholine in nervous tissues, and thus improve processes involved in learning and memorization of an active avoidance task.

Most particularly, according to the present invention, there are provided compounds of the formula

where Q is

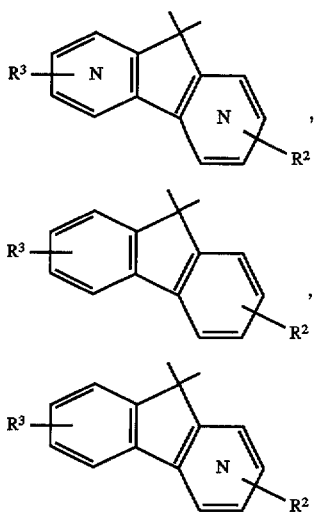

$R^1$ is 4-,3-, or 2-pyridyl, pyrimidyl, pyrazinyl, or fluoro-4-pyridyl;

$R^2$ and $R^3$ are independently H, F, Cl, Br, $-NO_2$, $-OH$, $-R^4$, $-OR^4$, $-CO_2R^4$, $-COR^4$, $-CONH_2$, $-CONHR^4$, $-CONR^4R^{4'}$, $-S(O)m-R^4$, $-NH_2$, $-CF_3$, $-NHR^4$, $-NR^4R^{4'}$;

$R^4$ and $R^{4'}$ are independently H, alkyl of 1 to 4 carbons, $-CH_2Phe-W$ or $Phe-W$;

Phe is a phenyl group;

$R_5$ is $-(CH_2)_n-Y$ or $-OCOR^4$;

Y is H, OH, $NH_2$, $NHR^4$, $NR^4R^4$, $NHCOR^4$, $NHCO_2R^4$, $NHS(O)_2R^4$; F, Cl, Br, $OR^4$, $S(O)_mR^4$, $-CO_2H$, $-CO_2R^4$, $-CN$, $-CONR^4R^{4'}$, $-CONHR^4$, $-CONH_2$, $-COR^4$; $-CH=CHCO_2R^4$, $-OCOR^4$, Phe, Phe—W, $-C\equiv CCO_2R^4$, $-CH=CHR^4$, or $-C\equiv C-R^4$;

W is F, Cl, Br, $R^4$, $-OR^4$, $NO_2$, $NH_2$, $NHR^4$, $NR^4R^4$, $-CN$, or $-S(O)_m-R^4$;

m is 0, 1 or 2;

n is 1 to 7;

and hydrates and physiologically suitable salts thereof.

This invention also relates to pharmaceutical compositions comprising a suitable pharmaceutical carrier and an amount of one or more of the above-described compounds effective to treat cognitive or neurological dysfunction. Still further, this invention relates to a method of treating cognitive or neurological dysfunction in a mammal comprising administering to the mammal a therapeutically effective amount of one or more of the above-described compounds.

Detailed Description of the Invention

Preferred Embodiments

Preferred compounds of this invention are those compounds of Formula I where, together or independently:

$R^1$ is 4-pyridyl, 4-pyrimidyl, or 2-fluoro-4-pyridyl;

$R_5$ is $-(CH_2)_n-Y$;

Y is $-CO_2R_4$, $-CN$, $-CONHR^4$, $-NHCOR^4$, $-NHCO_2R^4$, $-CH=CHCO_2R^4$, or $-OCOR^4$;

$R^2$ and $R^3$ are independently H, F, Cl, Br, OH, $R^4$, $-OR^4$, $-CO^2R^4$, $-COR^4$, $-CONH_2$, $-CONHR^4$, $-CONR^4R^{4'}$ or $-S(O)_mR^4$;

and $R^4$ and $R^{4'}$ are independently alkyl of 1 to 4 carbon atoms.

More preferred compounds of this invention are those preferred compounds above where, additionally, together or independently:

n is 1 to 4;

and $R^2$ and $R^3$ are independently H, F, Cl, Br, $CH_3$ or $-CO_2R^4$.

Specifically preferred compounds of Formula I are:
(a) 9-(4-Pyridinylmethyl)-9H-cyclopenta[2,1-B:3,4-B']-dipyridine-9-acetic Acid Ethyl Ester
(b) 9-(4-Pyridinylmethyl)-9H-cyclopenta[2,1-B:3,4-B']-dipyridine-9-butanoic Acid Ethyl Ester Hydrochloride Hemihydrate
(c) 9-(4-Pyridinylmethyl)-9H-cyclopenta[2,1 -B:3,4-B']-dipyridine-9-pentanenitrile
(d) 4-[9-(4-Pyridinylmethyl)-9H-fluoren-9-yl]-2-butenoic Acid Ethyl Ester Dihydrochloride
(e) 5-(4-Pyridinylmethyl)-5H-cyclopenta[2,1-B:3,4-B']-dipyridine-5-ethanol Acetate (Ester)
(f) 9-(4-Pyridinylmethyl)-9H-fluoren-9-acetic Acid Ethyl Ester Hydrochloride
(g) 9-(4-Pyridinylmetyl)-9H-fluoren-9-butanamide Hemihydrate
(h) 9-[(2-Fluoro-4-pyridinyl)methyl]-9H-cyclopenta[2,1-B:3.4-B')-dipyridine-9-butanoic Acid Ethyl Ester para-Toluenesulfonate Hemidydrate.

It should be recognized that the above-identified groups of compounds are preferred embodiments of this invention, but that their description herein is in no way intended to limit the overall scope of this invention.

Synthesis

Most of the compounds of this invention can be synthesized by the sequence shown in Scheme 1. A phenanthrene, azaphenanthrene or diazaphenanthrene is treated with alkaline potassium permanganate to produce the corresponding fluorenone, azafluorenone, or diazafluorenone. The resulting ketone is reacted with a picoline ($R^1$—$CH_3$) to give the carbinol ($R^1$—$CH_2$—Q—OH) which is dehydrated to the olefin ($R^1$—CH=Q), which is reduced to $R^1$—$CH^2$—Q—H. Generally, compounds $R^1$—$CH_2$—Q—H are treated with a base, in an appropriate aprotic solvent and temperature, to generate an anion (R¹—CH₂—Q:). The resulting anion is then alkylated with an appropriate aklyl halide (R⁵—Hal) to give the desired compounds (R¹—CH₂—Q—R⁵).

Scheme I.

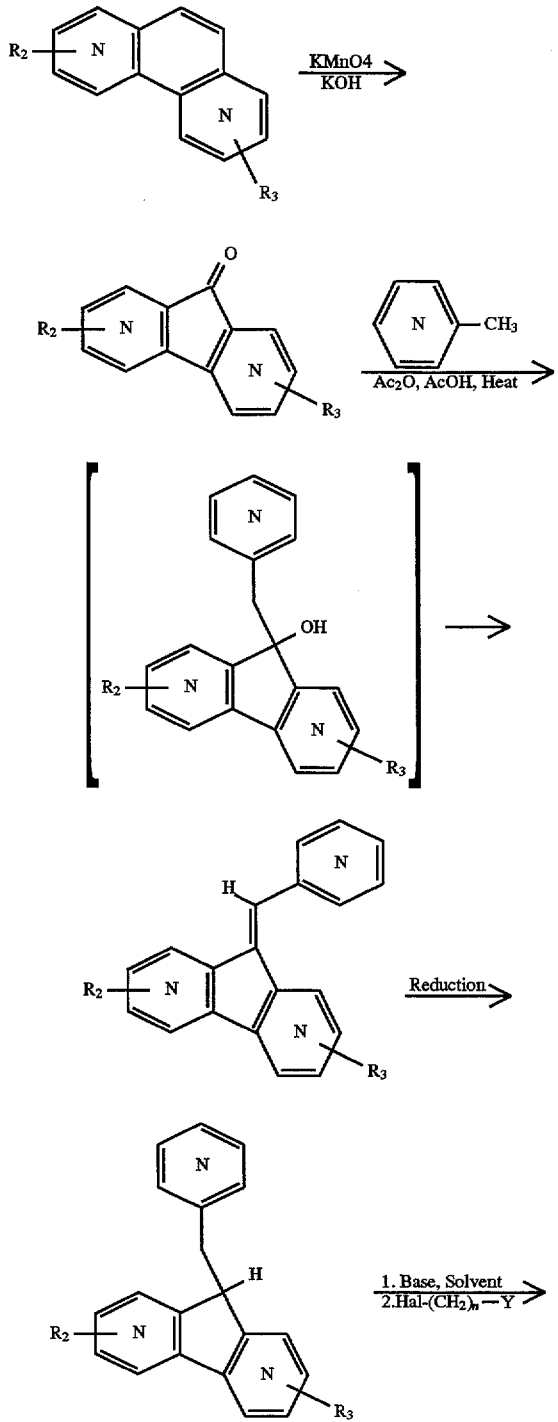

-continued
Scheme I.

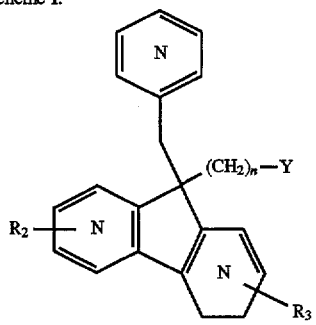

Suitable bases for forming the anion include, but are not limited to, sodamide, lithium diisopropylamide (LDA), sodium hydride, potassium tert-butoxide, sodium alkoxide, potassium alkoxide, potassium hydride, lithium 2, 2, 6, 6-tetramethylpiperidide, butyl lithium, sec-butyl lithium, tert- butyl lithium, and lithium-sodium-, or potassium hexamethyldisilazide. The reaction can be conducted in an aprotic solvent, generally in an ether, such as but not limited to, tetrahydrofuran (THF), dioxane, glyme, diglyme, or diethyl ether. Additionally, the reaction can be run in dimethylformamide or dimethylacetamide. However, if R¹—CH₂—Q—H is soluble in a nonpolar solvent, the reaction can be carried out in a hydrocarbon solvent such as hexanes, heptane, cyclohexane, methylcyclohexane, benzene or toluene. Depending on the strength of the base, the reactions can be conducted at a temperature from about −78° C. to solvent reflux temperature.

Typically, a 9-picolyl-diazafluorene, -fluorene, or an -azafluorene is dissolved or suspended in dry THF, cooled to about 0° C., treated with about 1.1 equivalents of sodium hydride, stirred for about 10 to 60 minutes under an inert gaseous environment, and treated dropwise with a solution of the alkylating agent. The reaction is stirred in the cold for about one hour, and at ambient temperature until no starting material can be detected by chromatographic methods. The reaction mixture is concentrated at reduced pressure, and the residue is partitioned between water and methylene chloride. The organic phase is washed with water and brine, dried over anhydrous magnesium sulfate, filtered, and concentrated at reduced pressure. Depending on the purity, the compounds of this invention may be collected as an oil, gum, or amorphous solid; or recrystallized from an appropriate solvent system; or further purified by chromatographic, sublimation, or distillation processes. The compounds may also exist as the 'free base' or as an acid addition salt formed from pharmaceutically acceptable acids. Additionally, compounds of Formula I may exist as racemates, diastereomeric mixtures, or their optically pure isomers.

Other representative compounds of this invention can be synthesized by converting one R₅ Y-group to another, as in the case of an ester (Y═CO₂R⁴) being converted to the corresponding acid(Y═CO₂H) or alcohol (Y═OH) which can be further converted to an ether (Y═OR⁴) or the 'reverse ester' (Y═O—COR⁴). For such a case, the ester can be saponified to give the acid (Y═CO₂H) which can be reduced to the alcohol. Alternatively, the ester can be directly reduced to the alcohol. An alternative approach to the 'reverse ester' compounds [Y=—OC(=O)R⁴], can be initiated with the ester, which can be reduced to the alcohol, which can be subsequently acylated with an acid halide or anhydride, or by coupling the alcohol to an acid using dicyclohexylcarbodiimide, carbonyl diimidazole, or some other coupling agent.

A nitrile can be hydrated to the corresponding amide using the procedure described by Noller, Org. Syn, Coll. Vol. II, p. 586. The same amide can be prepared from the corresponding ester by saponification, activation of carboxyl, and reaction with ammonia. By substituting primary or secondary amines for ammonia, other amides of this invention may be prepared. The corresponding amines can be obtained by reduction of the amides.

The compounds of the invention and their synthesis are further illustrated by the following examples and preparations. All temperatures are in degrees Celsius.

Preparation 1

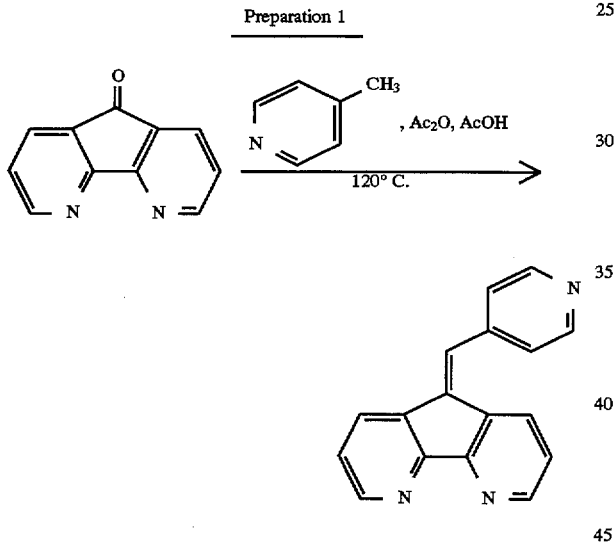

5-(4-Pyridinylmethylene)-5H-cyclopenta[2,1-B:3,4-B']-dipyridine.

A mixture of 4,5-diazafluorenone (10.0 g, 54 mmol), acetic acid (22.9 ml, 400 mmol), acetic anhydride (20.7 ml, 219 mmol), and 4-picoline (20.4 g, 219 mmol) was heated under reflux conditions for 13 h, and allowed to cool to room temperature. The mixture was diluted with 17 ml water and neutralized with 50% NaOH to pH 7.0. Additional water was added (50 ml) and the mixture was extracted with 6×50 ml CH₂Cl₂. The organic phase was washed with 1N NaOH and brine, dried over MgSO₄, filtered, and concentrated in vacuo. The residue was recrystallized from CHCl₃-Hexanes to give the desired product in 68% (9.4g) yield; mp 218° C. dec.

Preparation 2

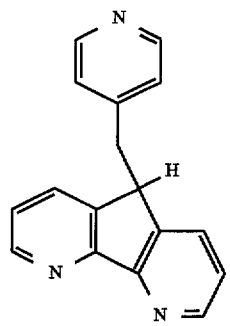

9-(4-Pyridinylmethyl)-9H-cyclopenta[2,1 -B:3,4-B]-dipyridine.

A solution of 5-(4-pyridinylmethylene)-5H- cyclopenta [2,1-B:3,4-B']-dipyridine (2.54 g, 10 mmol) in 35 ml MeOH was cooled in an ice bath and treated with NaBH₄ (1.5 equiv) and stirred in the cold until no starting olefin was evidenced by thin layer chromatography (TLC) (CHCl₃-MeOH,9:1). The mixture was diluted with 200 ml water and extracted with 3×50 ml CH₂Cl₂. The organic layer was washed with 5% NaHCO₃, water, and brine; dried over MgSO₄; filtered, and concentrated in vacuo. The residue was recrystallized from CHCl₃-Hexanes to give the desired product in 69% yield, mp 183° C. dec.

EXAMPLE 1

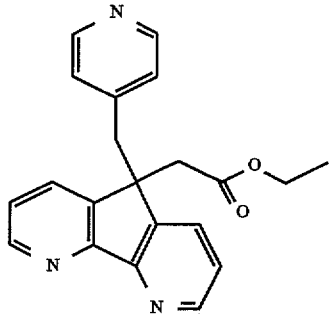

9-(4-Pyridinylmethyl)-9H-cyclopenta[2,1-B:3,4-B]-dipyridine-9-acetic Acid Ethyl Ester A slurry of NaH (21.7 mg, 0.9 mmol) in 20 ml dry THF, containing 1 ml dry DMF, was cooled in an ice bath and treated with the compound prepared in Preparation 2. The mixture was stirred in the ice bath for 30 minutes and treated with ethyl 2-bromoacetate (105 uL, 0.9 mmol). The mixture was stirred in the ice bath for 30 minutes and at room temperature for 16 hours. The reaction mixture was poured into 50 ml cold water and extracted with 3×20 ml CH₂Cl₂. The organic phase was washed with brine, dried over anhydrous MgSO₄, filtered, and concentrated in vacuo. The residue was column chromatographed on silica gel using CHCl₃-MeOH (9:1), and appropriate fractions were combined and evaporated to dryness (251 mg). The residue was recrystallized from hexane-CHCl₃ to give the desired product in 46% (130 mg) yield; mp 163°–165° C.; IR(KBr):

C=O @1737 cm$^{-1}$; NMR(CDCl$_3$ TMS):δ 0.94 (t, 3H, CH$_3$), 3.02 (s, 2H, CH$_2$), 3.42 (s, 2H, CH$_2$), 3.89 (q, 2H, OCH$_2$), [6.63(dd, 2H, J=4.5, 1.5 Hz), 7.31 (dd, 2H, J=7.7), 7.82 (dd, 2H, J=7.7, 1.5 Hz), 8.25 (d, 2H, J=5.9, 1.5 Hz), 8.69 (dd, 2H, J=4.7, 1.5 Hz) aromatic], mass spec m/e 346(M+1); Anal calcd for C$_{21}$H$_{19}$N$_3$O$_2$, MW 345.15: C, 73.01; H, 5.55; N, 12.17. Found: C, 72.87; H, 5.40; N, 12.08.

EXAMPLE 2

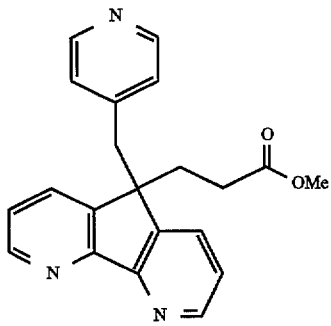

9-(4-Pyridinylmethyl)-9H-cyclopenta[2,1-B:3,4-B]-dipyridine-9-propanoic Acid Methyl Ester By substituting methyl 3-bromopropionate in Ex. 1, the desired product was obtained in 100% yield; mp 173°–174° C.

EXAMPLE 3

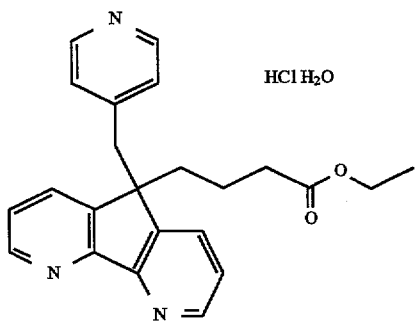

9-(4-Pyridinylmethyl)-9H-cyclopenta[2,1-B:3,4-B]-dipyridine-9-butanoic Acid Methyl Ester Hydrochloride Hemihydrate By substituting ethyl 4-bromobutyrate in Ex. 1, the desired product was obtained in 47% yield; mp 218°–228° C.

EXAMPLE 4

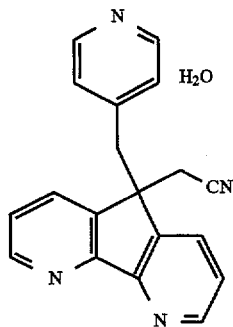

5-(4-Pyridinylmethyl)-5H-cyclopenta[2,1-B:3,4-B]-dipyridine-5-acetonitrile Hemihydrate By substituting 2-bromoacetonitrile in Ex. 1, the desired product was obtained in 62% yield; mp 60°–65° C.

EXAMPLE 5

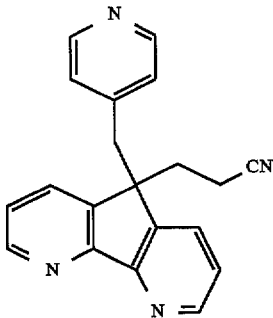

5-(4-Pyridinylmethyl)-5H-cyclopenta[2,1-B:3,4-B]-dipyridine-5-propanenitrile

By substituting 3-bromopropanenitrile in Ex. 1, the desired product was obtained in 30% yield; mp 205°–206° C.

EXAMPLE 6

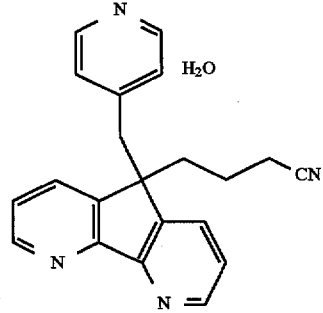

5-(4-Pyridinylmethyl)-5H-cyclopenta[2,1-B:3,4-B]-dipyridine-5-butanenitrile Hemihydrate By substituting 4-bromobutanenitrile in Ex. 1, the desired product was obtained in 93% yield; mp 96°–110° C.

EXAMPLE 7

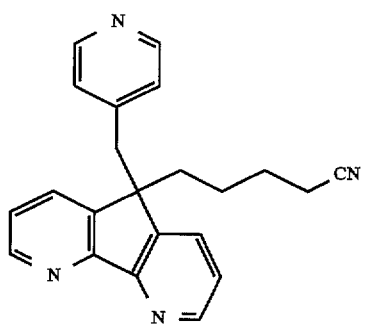

9-(4-Pyridinylmethyl)-9H-cyclopenta[2,1-B:3,4-B]-
dipyridine-9-pentanenitrile

By substituting 5-bromopentanenitrile in Ex. 1, the desired product was obtained in 65% yield; mp 190°–191 °C.

EXAMPLE 8

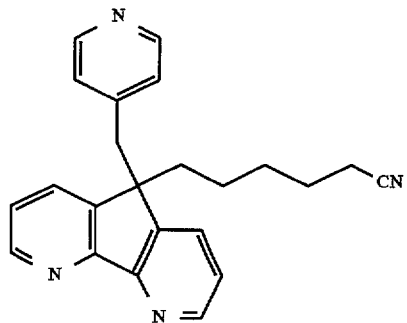

5-(4-Pyridinylmethyl)-5H-cyclopenta[2,1-B:3,4-B]-
dipyridine-5-hexanenitrile

By substituting 6-bromohexanenitrile in Ex. 1, the desired product was obtained in 44% yield; mp 151°–152° C.

EXAMPLE 9

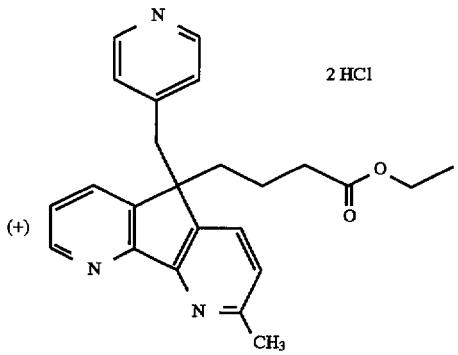

(+)-2-Methyl-5-(4-pyridinylmethyl)-5H-cyclopenta
[2,1-B:3,4-B]-dipyridine-5-butanoic Acid Ethyl
Ester Dihydrochloride By substituting ethyl 4-iodobutyrate and "3-methyl-4,5-diazafluorene" in Ex. 1, the corresponding racemate was obtained. The racemate was subjected to chiral HPLC to separate the enantiomers. The (+)-isomer was obtained in 71% yield; mp 115°–120° C., $[\alpha]^{25}D$ +12.75° (c,0.20, H$_2$O).

EXAMPLE 10

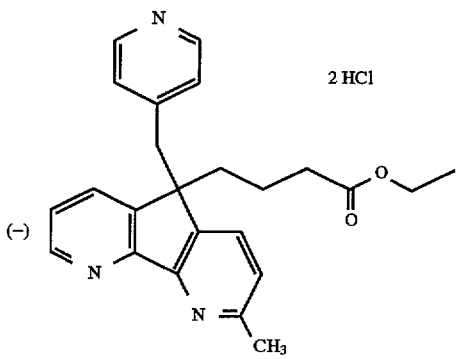

(−)-2-Methyl-5-(4-pyridinylmethyl)-5H-cyclopenta
[2,1-B:3,4-B]-dipyridine-5-butanoic Acid Ethyl
Ester Dihydrochloride By substituting ethyl-iodobutyrate and 3-methyl-4,5 diazafluorene in Ex. 1, the corresponding racemate was obtained. The racemate was subjected to chiral HPLC to separate the enantiomers. The (−)-isomer was obtained in 80% yield; mp 115°–120° C., $[\alpha]^{25}D$-12.26° (c,0.20, H$_2$O).

EXAMPLE 11

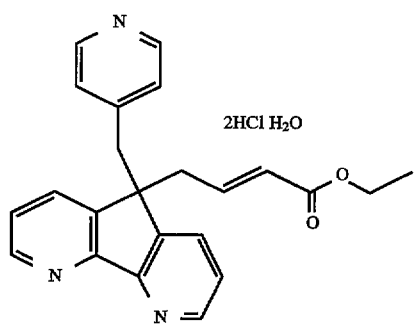

4-[9-(4-Pyridinylmethyl)-9H-fluoren-9-yl]-2-
butenoic Acid Ethyl Ester Dihydrochloride Hydrate By substituting ethyl 4-bmrnocrotonate in Ex. 1, the desired product was obtained in 57% yield; mp 200° C. dec.

EXAMPLE 12

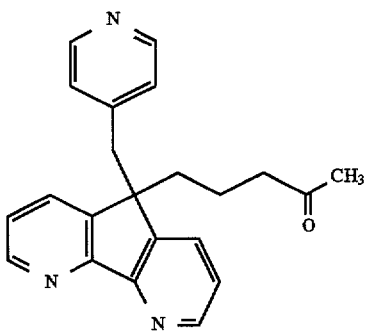

5-[5-(4-Pyridinylmeth-yl)-5H-cyclopenta[2,1-B:3,4-B]-diperidin-yl]-2-pentanone

By substituting 5-chloro-2-pentanone ethylene ketal in Ex. 1, the correspsonding new ketal was formed which was treated with aqueous hydrochloric acid to give the ketone that was in turn isolated as the free base in 63% yield; mp 146°–148° C.

EXAMPLE 13

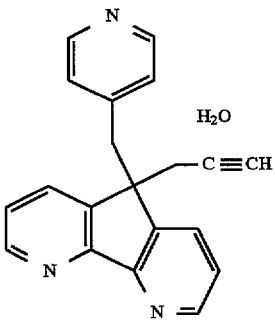

5-(2-Propynyl)-5-(4-pyridinylmethyl)-5H-cyclopenta[2,1-B:3,4-B]dipyridine Hydrate By substituting trimethylsilylpropargyl bromide in Ex. 1, followed by deprotection with 1N nBu4NF (tetrabutyl ammonium fluoride), and neutralization, the desired product was obtained in 80% yield; mp 183°–186° C.

EXAMPLE 14

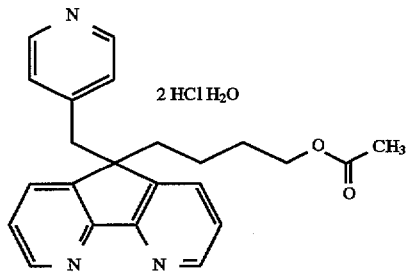

5-(4-Pyridinylmethyl)-5H-cyclopenta[2,1-B:3,4-B]-dipyridine-5-butanol Acetate (Ester) Dihydrochloride Hydrate By substituting 4-bromobutyl acetate in Ex. 1, the desired product was obtained in 59% yield; mp>200° C. dec.

EXAMPLE 15

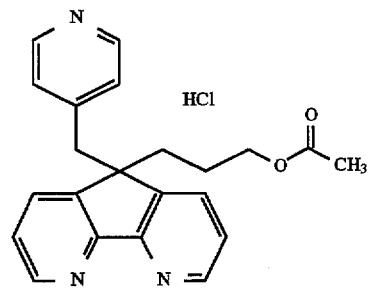

5-(4-Pyridinylmethyl)-5H-cyclopenta[2,1-B:3,4-B]-dipyridine-5-propanol Acetate (Ester) Hydrochloride By substituting 3-chloropropyl acetate in Ex. 1, the desired product was obtained in 22% yield; mp 218°–220° C.

EXAMPLE 16

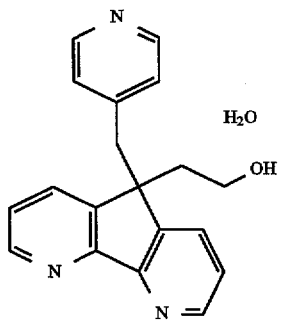

5-(4-Pyridinylmethyl)-5H-cyclopenta[2,1-B:3,4-B]-dipyridine-5-ethanol Hemihydrate By reducing the ester in Ex. 1 with lithium aluminum hydride, the desired product was obtained in 51% yield; mp 174°–177° C.

EXAMPLE 17

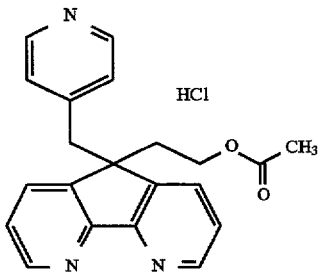

5-(4-Pyridinylmethyl)-5H-cyclopenta[2,1-B:3,4-B]-dipyridine-5-ethanol Acetate (Ester) Hydrochloride By acylating the alcohol in Ex. 16 with acetic anhydride in the presence of 4-(N,N-dimethylamino)-pyridine, the desired acetate was obtained in 37% yield; mp 220°–224° C.

Preparation 3

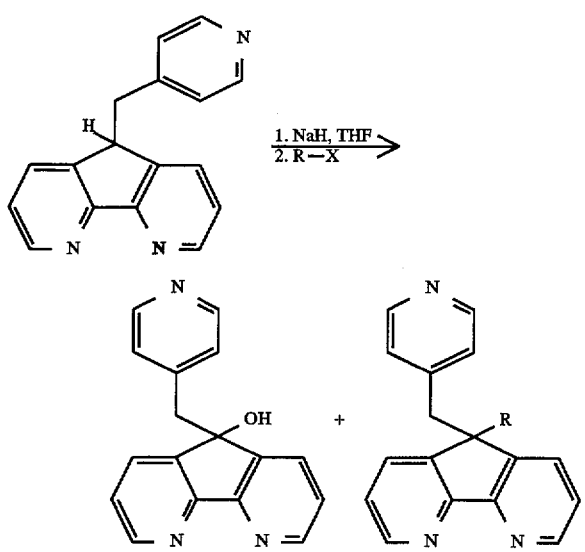

9-(4-pyridinylmethyl)-9H-cyclopenta[2,1-B:3,4-B]-
dipyridin-9-ol

In many of the alkylations of 9-(4-pyridinylmethyl)-9H-cyclopenta[2,1-B:3,4-B]-dipyridine (Prep.2), by forming the anion using NaH in THF, a byproduct was isolated and identifies as the carbinol.

EXAMPLE 18

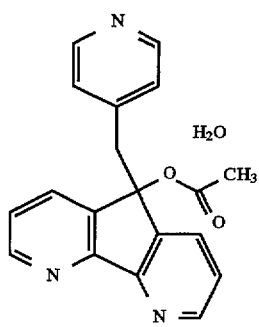

5-(4-Pyridinylmethyl)-5H-cyclopenta[2,1-B:3,4-B]-
dipyridine-5-ol Acetate (Ester) Hydrate By acylating 9-(4-pyridinylmethyl)-9H- cyclopenta[2,1-B:3,4-B]-dipyridin-9-ol with acetic anhydride in pyridine, the product was obtained in 82% yield; mp 181°–183° C.

EXAMPLE 19

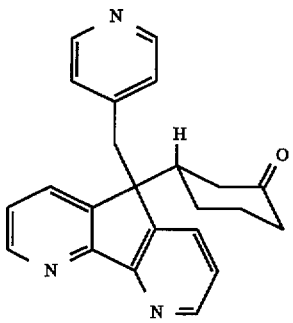

3-[5-(4-Pyridinylmethyl)-5H-cyclopenta[2,1-B:3,4-
B]dipyridin-5-yl]-9-cyclohexanone By reacting 9-(4-pyridinylmethyl-9H-cyclopenta[2,1-B:3,4-B]-dipyridine with cyclohexene-1-one under Michael Addition conditions, the desired product was obtained in 84% yield; mp 198°–199° C.

EXAMPLE 20

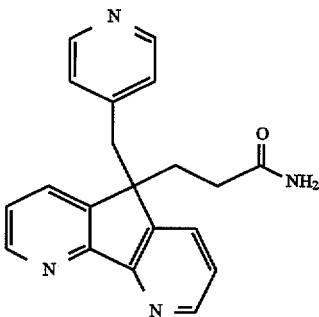

9-(4-Pyridinylmethyl)-9H-cyclopenta[2,1-B:3,4-B]-
dipyridine-9-propanamide

By reacting 9-(4-pyridinylmethyl)-9H-cyclopenta[2,1-B:3,4-B]-dipyridine with acrylamide under Michael Addition conditions, the desired product was obtained in 72% yield; mp 250° C. dec.

Preparation 4

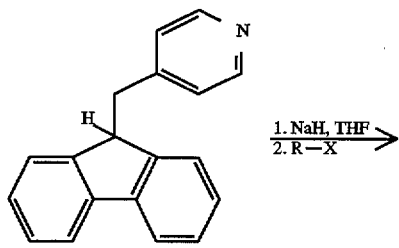

-continued
Preparation 4

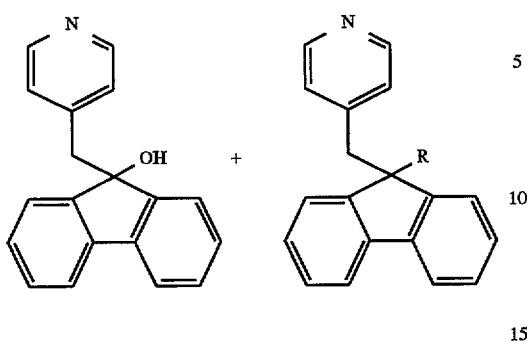

9-(4-pyridinylmethyl)-9H-fluoren-9-ol

By substituting 9-(4-pyridinylmethyl)-9H-fluorene in Prep 3, the corresponding carbinol was obtained.

EXAMPLE 21

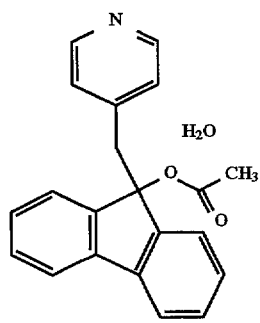

9-(4-Pyridinylmethyl)-9H-fluoren-9-ol Acetate Hydrate

By substituting 9-(4-pyridinylmethyl)-9H-fluoren-9-ol in Ex. 18, the desired product was obtained in 63% yield; mp 163°–165° C.

EXAMPLE 22

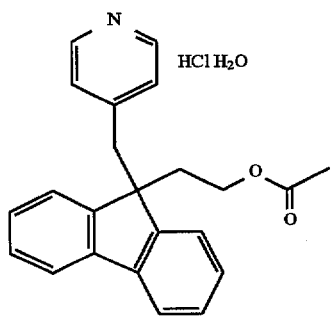

ethanol Acetate (ester) Hydrochloride Hydrate

By reacting 9-(4-pyridinylmethyl)9H-fluorene with 2-bromoethyl acetate as in Ex. 1, the desired product was obtained in 88% yield; mp 170°–172° C.

EXAMPLE 23

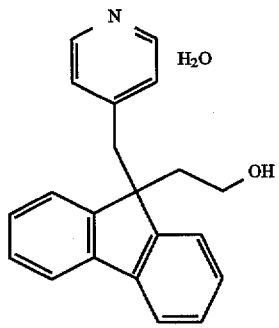

9-(4-Pyridinylmethyl)-9H-fluoren-9-ethanol Hemihydrate

By saponification of Ex. 22, the desired product was obtained in 100% yield; mp 150°–152° C.

EXAMPLE 24

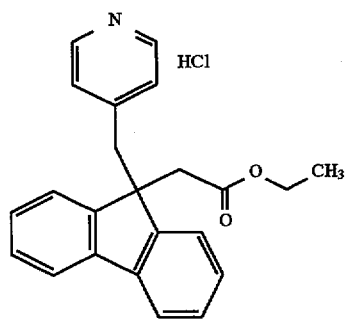

9-(4-Pyridinylmethyl)-9H-fluoren-9-acetic Acid Ethyl Ester Hydrochloride

By substituting ethyl 2-bromoacetate in Ex. 1, the desired product was obtained in 87% yield; mp 187°–189° C.

EXAMPLE 25

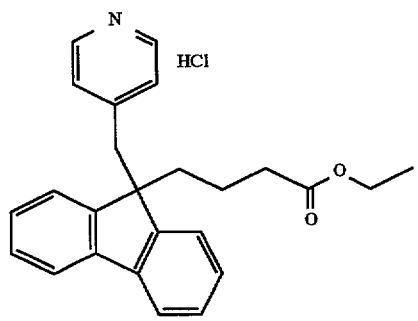

9-(4-Pyridinylmethyl)-9H-fluoren-9-butanoic Acid Ethyl Ester Hydrochloride

By substituting ethyl 4-bromobutyrate and 9-(4-pyridinylmethyl)-9H-fluorene in Ex. 1, the desired product was obtained in 35% yield; mp 178°–180° C.

EXAMPLE 26

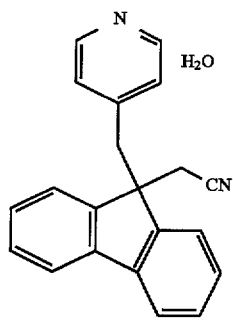

9-(4-Pyridinylmethyl)-9H-fluoren-9-acetonitrile
Hydrate

By substituting bromoacetonitrile and 9-(4-pyridinylmethyl)-9H-fluorene in Ex. 1, the desired product was obtained in 87% yield; mp 182°–184° C.

EXAMPLE 27

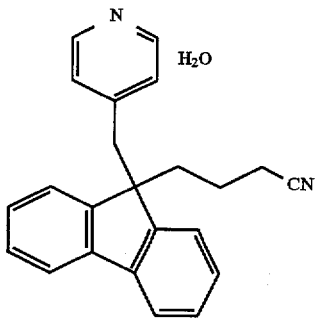

9-(4-Pyridinylmethyl)-9H-fluoren-9-butanenitrile
Hydrochloride Hydrate

By substituting 4-bromobutyronitrile and 9-(4-pyridinylmethyl)-9H-fluorene in Ex. 1, the desired product was obtained in 69% yield; mp 235°–237° C.

EXAMPLE 28

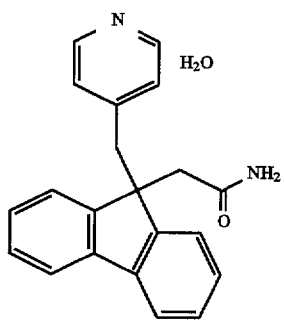

9-(4-Pyridinylmethyl)-9H-fluoren-9-acetamide
Hemihydrate

By substituting 9-(4-pyridinylmethyl)-9H-fluorene and α-bromoacetamide in Ex. 1, the desired product was isolated in 45% yield; mp 156°–158° C.

EXAMPLE 29

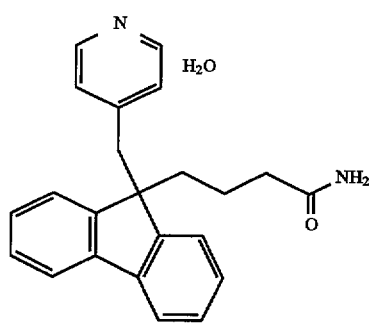

9-(4-Pyridinylmethyl)-9H-fluoren-9-butanamide
Hemihydrate

By substituting 4-bromobutyl acetamide and 9-(4-pyridinylmethyl)-9H-fluorene in Ex. 1, the product was obtained in 100% yield; mp 50°–52° C.

EXAMPLE 30

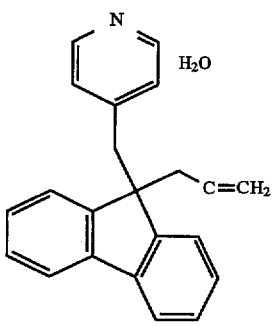

4-[9-(2-Propenyl)-9H-fluoren-9-ylmethyl]-pyridine
Hydrate

By substituting allyl bromide and 9-(4-pyridinylmethyl)-9H-fluorene in Ex. 1, the desired product was isolated in 40% yield; mp 56°–59° C.

EXAMPLE 31

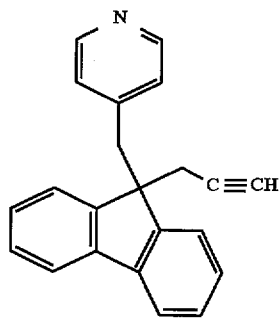

4-[5-(2-Propynyl)-5H-fluoren-5-ylmethyl]-pyridine

By substituting 9-(4-pyridinylmethyl)-9H-fluorene and propargyl bromide in Ex. 1, the desired product was obtained in 61% yield; mp 128°–130° C. dec.

EXAMPLE 32

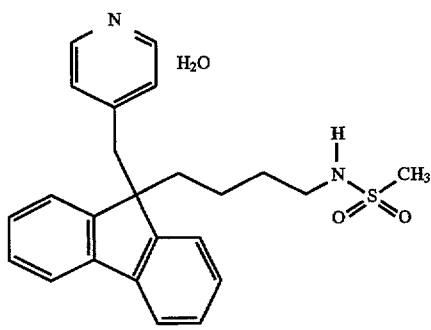

N-(4[5-(4-Pyridinylmethyl)-5H-fluoren-5-yl[-butyl)-methanesulfonamide Hydrate

By reducing Ex. 29 with LAH, followed by treatment with methanesulfonyl anhydride, using triethylamine as base, the desired product was obtained as a foam in 20% yield; NMR(CDCl3, TMS):δ 0.65 (m, 2H), 1.36 (m, 2H), 2.20 (q, 2H), 2.78 (s, 3H), 2.85 (q, 2H), 3.20 (s, 2H), 6.41 (dd, 2H), 7.27–7.39 (m, 6H), 7.52 (m, 2H), 8.07 (dd, 2H); mass spec m/e 407(M+1).

EXAMPLE 33

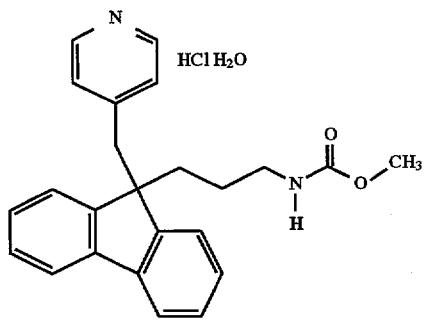

(3-[9-(4-Pyridinylmethyl)-9H-fluoren-9-yl]propyl)-carbamic Acid Methyl Ester Hydrochloride Hydrate By conducting a Hoffmann Degradation on Ex. 29, the corresponding product was obtained in 59% yield; mp 222°–225° C.

EXAMPLE 34

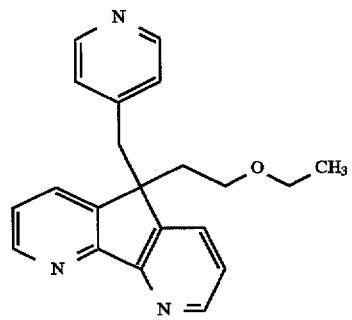

5-(2-Ethoxyethyl)-5-(4-pyridinylmethyl)-5H-cyclopenta[2,1-B:3,4-B]-dipyridine

By alkylating the alcohol in Ex. 16 with ethyl iodide, using NaH as base in DMF, the desired ether was obtained in 98% yield; mp 128°–129° C.

Preparation 5

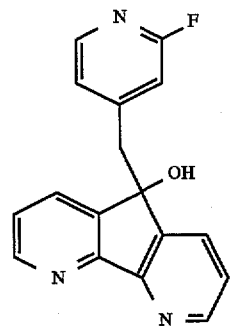

5-[(2-fluoro-4-pyridinyl)methyl]-5H-cyclopenta[2,1-B:3,4-B;]-dipyridin-5-ol

By substituting 5-[(2-fluoro-4-pyridinyl)methyl]-5H-cyclopenta[2,1-B:3,4-B;]-dipyridine in Prep 3, the desired carbinol was isolated.

EXAMPLE 35

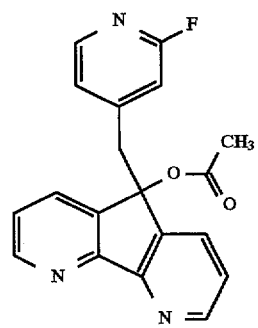

5-[(2-Fluoro-4-pyridinyl)methyl]-5H-cyclopenta[2,1-B:3,4-B;]-dipyridin-5-ol Acetate Ester By substituting 5-[(2-fluoro-4-pyridinyl)methyl]-5H-cyclopenta[2,1-B:3,4-B']-dipyridin-5-ol in Ex. 18, the desired product was obtained in 97% yield; mp 219°–221° C.

EXAMPLE 36

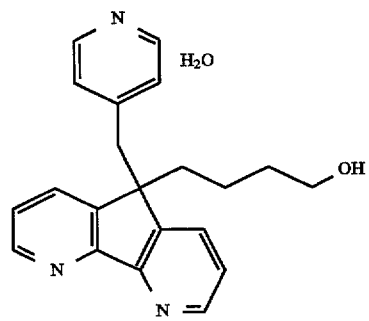

5-(4-Pyridinylmethyl)-5H-cyclopenta[2,1-B:3,4-B]-dipyridine-5-butanol Hemihydrate By reducing the ester in Ex. 3 with LAH, the desired alcohol was obtained in 51% yield; mp 53°–57° C.

EXAMPLE 37

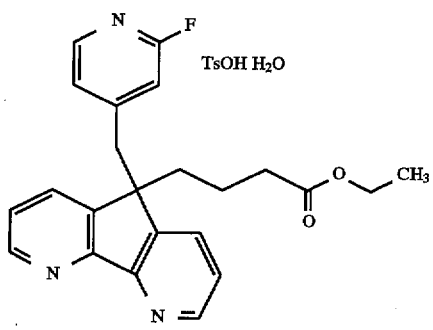

9-[(2-Fluoro-4-pyridinyl)methyl]-9H-cyclopenta[2,1-B:3,4-B]-dipyridine-9-butanoic Acid Ethyl Ester para-Toluenesulfonate Hemihydrate.

By substituting 9-(2-fluoro-4-pyridinylmethyl)-9H-cyclopenta[2,1-B:3,4-B]-dipyridine in Ex. 3, the desired product was obtained in 71% yield; mp 53°–59° C.

EXAMPLE 38

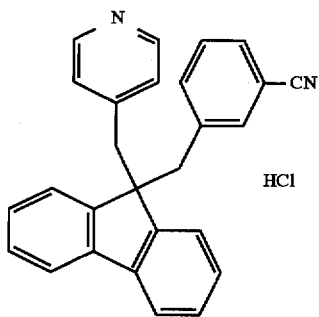

By substituting α-bromo-m-tolunitrile and 9-(4-Pyridinylmethyl)-9H-fluorene in Ex. 1, the desired product was obtained in 26% yield; mp 216°–219° C.

EXAMPLE 39

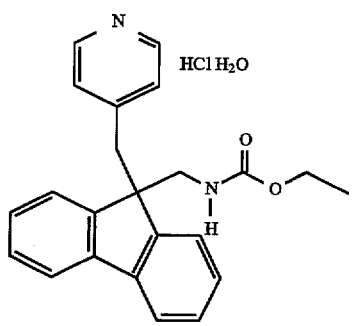

By conducting an Hoffmann Degradation ($Br_2$+NaOMe+MeOH) on the corresponding acetamide, which was obtained from the hydrolysis of the corresponding acetonitrile with NaOH+$H_2O_2$, the corresponding urethane was obtained. Upon acidification with HCl, the desired product was obtained as the hydrate hydrochloride salt in 29% yield; mp 193°–195° C.

By using the methods illustrated in the above example, the compounds in Table 1 can be prepared.

TABLE I

| Example | Q | R¹ | R² | R³ | R₅ |
|---|---|---|---|---|---|
| 40 | Fluorene | 2-F,4-Pyr | H | H | $CH_2$—Phe |
| 41 | 4,5-Diazafluorene | 4-Pyr | 8-$CO_2$Me | H | $(CH_2)_3$—$CO_2$Et |
| 42 | 4,5-Diazafluorene | 4-Pyr | 8-$CO_2$Me | H | $(CH_2)_4$—CN |
| 43 | 4,5-Diazafluorene | 4-Pyr | 8-$CO_2$Me | H | $CH_2$—(3-CN-Phe) |
| 44 | 4,5-Diazafluorene | 4-Pyr | 8-Cl | H | $(CH_2)_4$—CN |
| 45 | 4,5-Diazafluorene | 4-Pyr | 8-Br | H | $(CH_2)_4$—CN |
| 46 | 4,5-Diazafluorene | 4-Pyr | 8-F | H | $(CH_2)_4$—CN |
| 47 | 4,5-Diazafluorene | 4-Pyr | 8-$NO_2$ | H | $(CH_2)_4$—CN |
| 48 | 4,5-Diazafluorene | 4-Pyr | 8-OMe | H | $(CH_2)_4$—CN |

TABLE I-continued

| Example | Q | R¹ | R² | R³ | R₅ |
|---|---|---|---|---|---|
| 49 | 4,5-Diazafluorene | 4-Pyr | 8-SO₂Me | H | (CH₂)₄—CN |
| 50 | Fluorene | 2-F(-4-Pyr) | H | H | (CH₂)₃—CO₂Et |
| 51 | Fluorene | 2-F-(4-Pyr) | H | H | (CH₂)₄—CN |
| 52 | Fluorene | 2-F-(4-Pyr) | H | H | CH₂-(3-CN-Phe) |
| 53 | 3-Azafluorene | 2-F-(4-Pyr) | 8-Cl | H | (CH₂)₄—CN |
| 54 | 3-Azafluorene | 4-Pyr | 8-Br | H | (CH₂)₄—CN |
| 55 | 3-Azafluorene | 4-Pyr | 8-F | H | (CH₂)₄—CN |
| 56 | 3-Azafluorene | 4-Pyr | 8-NO₂ | H | (CH₂)₄—CN |
| 57 | 3-Azafluorene | 4-Pyr | 8-OMe | H | (CH₂)₄—CN |
| 58 | 3-Azafluorene | 4-Pyr | 8-SO₂Me | H | (CH₂)₄—CN |
| 59 | 3-Azafluorene | 4-Pyr | 8-Me | H | (CH₂)₄—CN |
| 60 | 3,6-Diazafluorene | 2-F-(4-Pyr) | 8-Cl | H | (CH₂)₄—CN |
| 61 | 3,6-Diazafluorene | 4-Pyr | 8-Br | H | (CH₂)₄—CN |
| 62 | 3,6-Diazafluorene | 4-Pyr | 8-F | H | (CH₂)₄—CN |
| 63 | 3,6-Diazafluorene | 4-Pyr | 8-NO₂ | H | (CH₂)₄—CN |
| 64 | 3,6-Diazafluorene | 4-Pyr | 8-OMe | H | (CH₂)₄—CN |
| 65 | 3,6-Diazafluorene | 4-Pyr | 8-SO₂Me | H | (CH₂)₄—CN |
| 66 | 3,6-Diazafluorene | 4-Pyr | 8-N(CH₃)₂ | H | (CH₂)₄—CN |
| 67 | 3,6-Diazafluorene | 4-Pyr | 8-CO₂Me | H | (CH₂)₄—CN |
| 68 | 2,7-Diazafluorene | 2-F-(4-Pyr) | 8-Cl | H | (CH₂)₄—CN |
| 69 | 2,7-Diazafluorene | 4-Pyr | 8-Br | H | (CH₂)₄—CN |
| 70 | 2,7-Diazafluorene | 4-Pyr | 8-F | H | (CH₂)₄—CN |
| 71 | 2,7-Diazafluorene | 4-Pyr | 8-NO₂ | H | (CH₂)₄—CN |
| 72 | 2,7-Diazafluorene | 4-Pyr | 8-OMe | H | (CH₂)₄—CN |
| 73 | 2,7-Diazafluorene | 4-Pyr | 8-SO₂Me | H | (CH₂)₄—CN |
| 74 | 2,7-Diazafluorene | 4-Pyr | 8-N(CH₃)₂ | H | (CH₂)₄—CN |
| 75 | 2,7-Diazafluorene | 4-Pyr | 8-CO₂Me | H | (CH₂)₄—CN |
| 76 | 4,5-Diazafluorene | 3-Pyr | H | H | (CH₂)₄—CN |
| 77 | 4,5-Diazafluorene | 2-Pyr | H | H | (CH₂)₄—CN |
| 78 | 4,5-Diazafluorene | 3-Pyr | H | H | (CH₂)₄—CN |
| 79 | 4,5-Diazafluorene | 2-Pyr | H | H | (CH₂)₄—CN |
| 80 | 4,5-Diazafluorene | 3-Pyr | H | H | (CH₂)₃—CO₂Et |
| 81 | 4,5-Diazafluorene | 2-Pyr | H | H | (CH₂)₃—CO₂Et |
| 82 | 4,5-Diazafluorene | 4-Pym | H | H | (CH₂)₃—CO₂Et |
| 83 | 4,5-Diazafluorene | 4-Pym | H | H | (CH₂)₄—CN |
| 84 | 4,5-Diazafluorene | 4-Pym | 8-Cl | H | (CH₂)₄—CN |
| 85 | 4,5-Diazafluorene | 4-Pym | 8-Br | H | (CH₂)₄—CN |
| 86 | 4,5-Diazafluorene | 4-Pym | 8-F | H | (CH₂)₄—CN |
| 87 | 4,5- | 4-Pym | 8-NO₂ | | |

TABLE I-continued

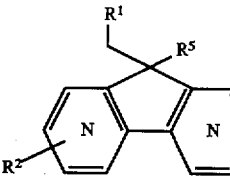

| Example | Q | R¹ | R² | R³ | R₅ |
|---|---|---|---|---|---|
| 88 | 4,5-Diazafluorene | 4-Pym | 8-OMe | H | $(CH_2)_4-CN$ |
| 89 | 4,5-Diazafluorene | 4-Pym | 8-SO$_2$Me | H | $(CH_2)_4-CN$ |
| 90 | 4,5-Diazafluorene | 4-Pym | 8-Me | H | $(CH_2)_4-CN$ |
| 91 | Fluorene | 4-Pyr | 2-Cl | 7-NO$_2$ | $(CH_2)_4-CN$ |
| 92 | Fluorene | 4-Pyr | 2-NH$_2$ | 7-NH$_2$ | $(CH_2)_4-CN$ |
| 93 | Fluorene | 4-Py | 2-NH$_2$ | 7-OMe | $(CH_2)_4-CN$ |
| 94 | Fluorene | 4-Py | 2-N(Me)$_2$ | H | $(CH_2)_4-CN$ |
| 95 | Fluorene | 2-F,4-Pyr | Br | H | $(CH_2)_3CO_2Et$ |
| 96 | Fluorene | 2-F,4-Pyr | Br | NO$_2$ | $(CH_2)_4CN$ |

(Pyr = pyridyl; Pym = pyrimidine; Py = pyrazine)

Biochemical Test Procedure

Neurotransmitter release assay

The neurotransmitter release activities of the compounds of this invention were determined as reported by Nickolson, et al., (1990) Drug Development Research, 19, 285–300 of a modification of the procedure described by Mulder, et al., Brain Res., 1974, 70, 372.

Male Wistar rats (Charles River) weighing 175–200 grams were used. The rats were housed for at least seven days before the experiment in animal facility under 12/12 hour light/dark cycle. Deionized water and standard rat chow (Purina) were available ad libitum.

Rats were decapitated and brains were dissected immediately. Slices (0.3 mm thick) from the parietal cortex were prepared manually using a recessed Lucite guide and subsequently cut into 0.25×0.25 mm squares.

Slices (approximately 100 mg wet weight) were incubated in 10 ml Krebs-Ringer medium (KR) containing NaCl (116 mM), KCl (3 mM), CaCl$_2$ (1.3 mM), MgCl$_2$ (1.2 mM), KH$_2$PO$_4$ (1.2 mM), Na$_2$SO$_4$ (1.2 mM), NaHCO$_3$ (25.0 mM), and glucose (11.0 mM), to which was added 10 uCi $^3$H-choline (specific activity approximately 35 Ci/mM; NEN) and 10 mM unlabeled choline had been added to give a final concentration of one micromole. The brain preparations were incubated for 30 min. at 37° C. under a steady flow of 95% O$_2$/5% CO$_2$. Under these conditions, part of the radioactivity choline taken up by the preparation was converted into radioactive acetylcholine (ACh) by the cholinergic nerve endings stored in synaptic vesicles, and released upon depolarization by high potassium ion (K+) containing media.

After labelling of the ACh stores, the slices were washed three times with non-radioactive KR medium and transferred to a superfusion apparatus to measure the drug effects on ACh release. The superfusion apparatus consisted of 10 thermostated glass columns of 5 mm diameter that were provided with GF/F glass fiber filters to support the slices (approximately 10 mg tissue/column). Superfusion was carried out in KR-medium (0.3 ml/min.) containing 10 mM hemicholine-3 (HC-3). The HC-3 prevents the reuptake of choline formed during the superfusion from phospholipids and released ACh, which would be converted into unlabeled ACh and released in preference to the pre-formed labelled ACh. The medium was delivered by a 25-channel peristaltic pump (Ismatec by Brinkman) and warmed to 37° C. in a thermostated stainless steel coil before entering the superfusion column. Each column was provided with a 4-way slider valve (Beckmann Instruments) which allowed rapid change of low to high K+/KR-medium, and with two 10-channel 3-way valves that were used to change from drug-free to drug-containing low and high K+/KR-medium.

After 15 min. of washout of non-specifically bound radioactivity, collection of 4 min. fractions was initiated. After three 4 min. collections, the original medium was changed to a KR-medium in which the KCl concentration had been increased to 25 mM (high K+medium) (S1). Depolarization-induced stimulation of release by high K+/KR-medium lasted for 4 min. Drug free low and high K+/KR-media were then substituted by drug- and vehicle-containing low- and high-K+/KR-medium, and superfusion was continued for three 4 min. collections with low K+/KR-medium, one 4 min. collection with high K+/KR-medium (S2), and two 4 min. collections with low K+/KR-medium.

Drug was added to the media by 100-fold dilutions of appropriate concentrations of the drug (in 0.9% saline) with either low- or high-K+/KR-medium.

All superfusion fractions were collected in liquid scintillation counting vials. After superfusion, the slices were removed from the superfusion columns and extracted with 1.0 ml of 0.1N HCl. Liquiscint (NEN) counting fluid (12 ml) was added to superfusion fractions and extracts, and the samples were counted in a Packard Tricarb Liquid Scintillation Counter. No corrections were made for quenching.

The ratio of S2/S1 (as compared to controls where no drug was present during S2) was a measure of the ability of the drug to enhance or depress stimulus-induced acetylcholine release. Per cent Acetylcholine (ACh) enhanced releases cause by 10 uM of drug using this assay are shown in Table II.

TABLE II

| Ex. | Q | R$^1$ | R$^5$ | % Yield | mp. °C. | % ACh Rel @ 10 uM |
|---|---|---|---|---|---|---|
| 1 | 4,5-Diazafluorene | 4-Pyr | $(CH_2)_1CO_2Et$ | 88 | 163–165 | 302 |
| 2 | 4,5 Diazafluorene | 4-Pyr | $(CH_2)_2CO_2Me$ | 100 | 173–174 | 119 |
| 3 | 4,5-Diazafluorene | 4-Pyr HCl H$_2$O | $(CH_2)_3(CO_2Et$ | 47 | 218–228 | 318 |
| 4 | 4,5-Diazafluorene | 4-Pyr H$_2$O | $(CH_2)_1$—CN | 62 | 60–65 | 95 |
| 5 | 4,5-Diazafluorene | 4-Pyr | $(CH_2)_2$—CN | 30 | 205–206 | 109 |
| 6 | 4,5-Diazafluorene | 4-Pyr H$_2$O | $(CH_2)_3$—CN | 93 | 96–110 | 165 |
| 7 | 4,5-Diazafluorene | 4-Pyr | $(CH_2)_4$—CN | 65 | 190–191 | 351 |
| 8 | 4,5-Diazafluorene | 4-Pyr | $(CH_2)_5$—CN | 44 | 151–152 | 175 |
| 9 | 3-Me-4,5-Diazafluorene | 4-Pyr 2HCl | (+)-$(CH_2)_3CO_2Et$ | 71 | 115–120 | 165 |
| 10 | 3-Me-4,5-Diazafluorene | 4-Pyr 2HCl | (−)-$(CH_2)_3CO_2Et$ | 80 | 115–120 | 155 |
| 11 | 4,5-Diazafluorene | 4-Pyr | CH$_2$—CH=CH—CO$_2$Et | 57 | 200–201 | 213 |
| 12 | 4,5-Diazafluorene | 4-Pyr | $(CH_2)_3$—COMe | 63 | 146–148 | 164 |
| 13 | 4,5-Diazafluorene | 4-Pyr 0.5H$_2$O | CH$_2$—C≡CH | 80 | 183–186 | 176 |
| 14 | 4,5-Diazafluorene | 4-Pyr 2HCl H$_2$O | $(CH_2)_4$—OAc | 59 | >200 dec | 152 |
| 15 | 4,5-Diazafluorene | 4-Pyr HCl | $(CH_2)_3$—OAc | 22 | 218–220 | 173 |
| 16 | 4,5-Diazafluorene | 4-Pyr 0.5H$_2$O | $(CH_2)_2$—OH | 51 | 174–177 | 106 |
| 17 | 4,5-Diazafluorene | 4-Pyr HCl | $(CH_2)_2$—OAc | 37 | 220–224 | 211 |
| 18 | 4,5-Diazafluorene | 4-Pyr 0.5H$_2$O | OAc | 82 | 181–183 | 101 |
| 19 | 4,5-Diazafluorene | 4-Pyr | 3-(O)-C$_6$H$_9$ | 84 | 198–199 | 112 |
| 20 | 4,5-Diazafluorene | 4-Pyr | $(CH_2)_2$—CONH$_2$ | 72 | 250 dec | 103 |
| 21 | Fluorene | 4-Pyr 0.25H$_2$O | OAc | 63 | 163–165 | 184 |
| 22 | Fluorene | 4-Pyr HCl H$_2$O | $(CH_2)_2$—OAc | 88 | 170–172 | 187 |
| 23 | Fluorene | 4-Pyr 0.5H$_2$O | $(CH_2)_2$—OH | 100 | 150–152 | 146 |
| 24 | Fluorene | 4-Pyr HCl | $(CH_2)_1$—CO$_2$Et | 87 | 187–189 | 204 |
| 25 | Fluorene | 4-Pyr HCl | $(CH_2)_3$—CO$_2$Et | 35 | 178–180 | 107 |
| 26 | Fluorene | 4-Pyr 0.2H$_2$O | $(CH_2)_1$—CN | 87 | 182–184 | 171 |
| 27 | Fluorene | 4-Pyr HCl 0.25 H$_2$O | $(CH_2)_3$—CN | 69 | 235–237 | 189 |
| 28 | Fluorene | 4-Pyr 0.5H$_2$O | $(CH_2)_1$—CONH$_2$ | 45 | 156–158 | 127 |
| 29 | Fluorene | 4-Pyr 0.75H$_2$O | $(CH_2)_3$—CONH$_2$ | 100 | 150–152 | 335 |
| 30 | Fluorene | 4-Pyr 0.2H$_2$O | CH$_2$—CH=CH$_2$ | 40 | 56–59 | 101 |
| 31 | Fluorene | 4-Pyr | CH$_2$—C#CH | 61 | 128–130 | 104 |
| 32 | Fluorene | 4-Pyr H$_2$O | $(CH_2)_4$—NHSO$_2$Me | 20 | foam | 118 |
| 33 | Fluorene | 4-Pyr HCl 0.25H$_2$O | $(CH_2)_3$—CO$_2$Me | 59 | 222–225 | 117 |
| 34 | 4,5-Diazafluorene | 4-Pyr | $(CH_2)_2$—OEt | 98 | 128–129 | 146 |
| 35 | 4,5-Diazafluorene | 2-F, 4-Pyr | OAc | 97 | 219–221 | 122 |
| 36 | 4,5-Diazafluorene | 4-Pyr 0.25H$_2$O | $(CH_2)_4$—OH | 51 | 53–57 | 149 |
| 37 | 4,5-Diazafluorene | 2-F, 4-Pyr TsOH 0.25H$_2$O | $(CH_2)_3$—CO$_2$Et | 71 | 53–59 | 196 |
| 38 | Fluorene | 4-Pyr HCl | CH$_2$-(3-CN—Phe) | 28 | 216–219 | 208 |
| 39 | Fluorene | 4-Pyr HCl H$_2$O | CH$_2$—NHCO$_2$Me | 29 | 193–195 | 160 |

Utility

The foregoing test results suggest that the compounds of this invention have utility in the treatment of cognitive disorders and/or neurological function deficits and/or mood and mental disturbances in patients suffering from nervous system disorders like Alzheimer's disease, Parkinson's disease, senile-dementia, multi-infarct dementia, Huntington's disease, mental retardation, Myasthenia Gravis, etc. In light of Cook, L., et al., Drug Development Research 19:301–314 (1990), Nickolson, V. J., et al., Drug Development Research 19:285–300 (1990), and DeNoble, V. J., et al., Pharmacology Biochemistry & Behavior, Vol. 36, pp. 957–961 (1990), all have shown by the above in vitro assay that the drug DuP 996, 3,3-bis(4-pyridinylmethyl)-1-phenylindolin-2-one, is useful in the treatment of cognition dysfunction.

Compounds of this invention can be administered to treat said deficiencies by any means that produces contact of the active agent with the agent's site of action in the body of a mammal. The compounds can be administered by any conventional means available for use in conjunction with pharmaceuticals either as individual therapeutic agent or in combination of therapeutic agents. They can be administered alone, but are generally administered with a pharmaceutical carrier selected on the basis of the chosen route of administration and standard pharmaceutical practice.

The dosage administered will vary depending on the use and known factors such as the pharmacodynamic character of the particular agent, and its mode and route of administration; the recipient's age, weight, and health; nature and extent of symptoms; kind of concurrent treatment; frequency of treatment; and the desired effect. For use in the treatment of said diseases or conditions, the compounds of this invention can be orally administered daily at a dosage of the active ingredient of 0.001 to 100 mg/kg of body weight. Ordinarily, a dose of 0.01 to 10 mg/kg/day in divided doses one to four times a day, or in sustained release formulation was effective in obtaining the desired pharmacological effect.

Dosage forms (compositions) suitable for administration contain from about 1 mg to about 100 mg of active ingredient per unit. In these pharmaceutical compositions, the active ingredient will ordinarily be present in an amount of about 0.5 to 95% by weight based on the total weight of the composition.

The active ingredient can be administered orally in solid dosage forms, such as capsules, tablets, and powders; or in liquid forms such as elixirs, syrups, and/or suspensions. The compounds for this invention can also be administered parenterally in sterile liquid dose formulations.

Gelatin capsules can be used to contain the active ingredient and a suitable carrier such as but not limited to lactose, starch, magnesium stearate, steric acid, or cellulose derivatives. Similar diluents can be used to make compressed tablets. Both tablets and capsules can be manufactured as sustained release products to provide for continuous release of medication over a period of time. Compressed tablets can be sugar coated or film coated to mask any unpleasant taste, or used to protect the active ingredients from the atmosphere, or to allow selective disintegration of the tablet in the gastrointestinal tract.

Liquid dosage forms for oral administration can contain coloring and flavoring agents to increase patient acceptance.

In general, water, pharmaceutically acceptable oils, saline, aqueous dextrose (glucose), and related sugar solutions and glycols, such as propylene glycol or polyethylene glycol, are suitable carriers for parenteral solutions. Solutions for parenteral administration preferably contain a water soluble salt of the active ingredient, suitable stabilizing agents, and if necessary, butter substances. Antioxidizing agents, such as sodium bisulfite, sodium sulfite, or ascorbic acid, either alone or in combination, are suitable stabilizing agents. Also used are citric acid and its salts, and EDTA. In addition, parenteral solutions can contain preservatives such as benzalkonium chloride, methyl- or propylparaben, and chlorobutanol.

Suitable pharmaceutical carriers are described in "Remington's Pharmaceutical Sciences", A. Osol, a standard reference in this field.

Useful pharmaceutical dosage-forms for administration of the compounds of this invention can be illustrated as follows:

Capsules

A large number of unit capsules are prepared by filling standard two-piece hard gelatin capsules each with 100 mg of powdered active ingredient, 150 mg lactose, 50 mg cellulose, and 6 mg magnesium stearate.

Soft Gelatin Capsules

A mixture of active ingredient in a digestible oil such as soybean, cottonseed oil, or olive oil is prepared and injected by means of a positive displacement was pumped into gelatin to form soft gelatin capsules containing 100 mg of the active ingredient. The capsules are washed and dried.

Tablets

A large number of tablets are prepared by conventional procedures so that the dosage unit was 100 mg of active ingredient, 0.2 mg of colloidal silicon dioxide, 5 mg of magnesium stearate, 275 mg of microcrystalline cellulose, 11 mg of starch, and 98.8 mg lactose. Appropriate coatings may be applied to increase palatability or delayed absorption.

The compounds of this invention may also be used as reagents or standards in the biochemical study of neurological function, dysfunction, and disease.

What is claimed is:

1. A compound of the formula $$\begin{array}{c} R^1 \\ | \\ Q-R^5 \end{array}$$

where Q is selected from the group consisting of

[structure with $R^2$ and $R^3$ on fluorene with N]

or

[structure with $R^2$ and $R^3$ on fluorene] -continued $R^1$ is selected from the group consisting of 4-, 3-, or 2-pyridyl, pyrimidyl, pyrazinyl, and fluoro-4-pyridyl;

$R^2$ and $R^3$ are independently selected from the group consisting of H, F, Cl, Br, $-NO_2$, $-OH$, $R^4$, $-OR^4$, $-CO_2R^4$, $-COR^4$, $-CONH_2$, $-CONHR^4$, $-CONR^4R^{4'}$, $-S(O)_m-R^4$, $-NH_2$, $-CF_3$, $-NHR^4$, and $-NR^4R^{4'}$;

$R^4$ and $R^{4'}$ are independently selected from the group consisting of H, alkyl of 1 to 4 carbons, $-CH_2$Phe-W and $-$Phe-W;

Phe is a phenyl group;

$R^5$ is selected from the group consisting of $-(CH_2)_n-Y$ and $-OCOR^4$;

Y is selected from the group consisting of H, $-OH$, $-NH_2$, $-NHR^4$, $-NR^4R^{4'}$, $-NHCO_2R^4$, $-NHS(O)_2R^4$, F, Cl, Br, $-OR^4$, $-S(O)_mR^4$, $-CO_2H$, $-CO_2R^{4'}$, $-CN$, $-CONR^4R^{4'}$, $-CONHR^4$, $-CONH_2$, $-COR^4$, $-CH=CHCO_2R^4$, $-OCOR^4$, -Phe, -Phe-W, $-C\equiv CCO_2R^4$, $-CH=CHR_4$, and $-C\equiv C R^4$;

W is selected from the group consisting of F, Cl, Br, $-NO_2$, $-NH_2$, and $-CN$;

m is 0, 1 or 2;

n is 1 to 7;

and hydrates and physiologically suitable salts thereof.

2. A compound of claim 1 where $R^1$ is selected from the group consisting of 4-pyridyl, 4-pyrimidyl, and 2-fluoro-4-pyridyl.

3. A compound of claim 1 where $R_5$ is $-(CH_2)_n-Y$.

4. A compound of claim 3 where Y is selected from the group consisting of $-CO_2R^4$, $-CN$, $-CONHR^4$, $-NHCOR^4$, $-NHCO_2R^4$, $-CH=CHCO_2R^4$, and $-OCOR^4$.

5. A compound of claim 1 where $R^2$ and $R^3$ are independently selected from the group consisting of H, F, Cl, Br, OH, $-R^4$, $-OR^4$, $-CO_2R^4$, $-COR^4$, $-CONH_2$, $-CONHR^4$, $-CONR^4R^{4'}$ and $-S(O)m^{R4}$, and $R^4$ and $R^{4'}$ are independently selected from the group consisting of alkyl of 1 to 4 carbon atoms.

6. A compound of claim 2 where $R_5$ is $-(CH_2)_n-Y$ and n is 1 to 4.

7. A compound of claim 6 where Y is selected from the group consisting of $-CO_2R^4$, $-CN$, $-CONHR^4$, $-NHCOR^4$, $-NHCO_2R^4$, $-CH=CHCO_2R^4$, and $-OCOR^4$.

8. A compound of claim 6 where $R^2$ and $R^3$ are independently selected from the group consisting of H, F, Cl, Br, $-CH_3$ and $-CO_2R^4$, and $R^4$ is selected from the group consisting of alkyl of 1 to 4 carbons.

9. The compound of claim 1 which is 4-[9-(4-Pyridinylmethyl)-9H-fluoren-9-yl]-2-butenoic Acid Ethyl Ester Dihydrochloride.

10. The compound of claim 1 which is 9-(4-Pyridinylmethyl)-9H-fluoren-9-acetic Acid Ethyl Ester Hydrochloride.

11. The compound of claim 1 which is 9-(4-Pyridinylmethyl)-9H-fluoren-9-butanamide Hemihydrate.

12. A pharmaceutical composition comprising a suitable pharmaceutical carrier and a therapeutically effective amount of a compound of claim 1.

13. A pharmaceutical composition comprising a suitable pharmaceutical carrier and a therapeutically effective amount of a compound of claim 2.

14. A pharmaceutical composition comprising a suitable pharmaceutical carrier and a therapeutically effective amount of a compound of claim 3.

15. A pharmaceutical composition comprising a suitable pharmaceutical carrier and a therapeutically effective amount of a compound of claim 4.

16. A pharmaceutical composition comprising a suitable pharmaceutical carrier and a therapeutically effective amount of a compound of claim 5.

17. A pharmaceutical composition comprising a suitable pharmaceutical carrier and a therapeutically effective amount of a compound of claim 6.

18. A pharmaceutical composition comprising a suitable pharmaceutical carrier and a therapeutically effective amount of a compound of claim 7.

19. A pharmaceutical composition comprising a suitable pharmaceutical carrier and a therapeutically effective amount of a compound of claim 8.

20. A pharmaceutical composition comprising a suitable pharmaceutical carrier and a therapeutically effective amount of a compound of claim 9.

21. A pharmaceutical composition comprising a suitable pharmaceutical carrier and a therapeutically effective amount of a compound of claim 10.

22. A pharmaceutical composition comprising a suitable pharmaceutical carrier and a therapeutically effective amount of a compound of claim 11.

23. A method for the treatment of cognitive or neurological dysfunction in a mammal comprising administering to the mammal a therapeutically effective amount of a compound of claim 1.

24. A method for the treatment of cognitive or neurological dysfunction in a mammal comprising administering to the mammal a therapeutically effective amount of a compound of claim 2.

25. A method for the treatment of cognitive or neurological dysfunction in a mammal comprising administering to the mammal a therapeutically effective amount of a compound of claim 3.

26. A method for the treatment of cognitive or neurological dysfunction in a mammal comprising administering to the mammal a therapeutically effective amount of a compound of claim 4.

27. A method for the treatment of cognitive or neurological dysfunction in a mammal comprising administering to the mammal a therapeutically effective amount of a compound of claim 5.

28. A method for the treatment of cognitive or neurological dysfunction in a mammal comprising administering to the mammal a therapeutically effective amount of a compound of claim 6.

29. A method for the treatment of cognitive or neurological dysfunction in a mammal comprising administering to the mammal a therapeutically effective amount of a compound of claim 7.

30. A method for the treatment of cognitive or neurological dysfunction in a mammal comprising administering to the mammal a therapeutically effective amount of a compound of claim 8.

31. A method for the treatment of cognitive or neurological dysfunction in a mammal comprising administering to the mammal a therapeutically effective amount of a compound of claim 9.

32. A method for the treatment of cognitive or neurological dysfunction in a mammal comprising administering to the mammal a therapeutically effective amount of a compound of claim 10.

33. A method for the treatment of cognitive or neurological dysfunction in a mammal comprising administering to the mammal a therapeutically effective amount of a compound of claim 11.

* * * * *